United States Patent [19]

Sorensen

[11] Patent Number: 5,102,505
[45] Date of Patent: Apr. 7, 1992

[54] MIXED ALDEHYDE PRODUCT SEPARATION BY DISTILLATION

[75] Inventor: Kirk D. Sorensen, Charleston, W. Va.

[73] Assignee: Union Carbide Chemicals & Plastics Technology Corporation, Danbury, Conn.

[21] Appl. No.: 611,080

[22] Filed: Nov. 9, 1990

[51] Int. Cl.[5] .......................... B01D 3/14; C07C 45/82
[52] U.S. Cl. ....................................... 203/91; 203/94; 203/DIG. 19; 568/449; 568/492
[58] Field of Search .................. 203/91, DIG. 19, 99, 203/94; 568/492, 449

[56] References Cited

U.S. PATENT DOCUMENTS

| | | | |
|---|---|---|---|
| 4,013,521 | 3/1977 | Scott | 203/DIG. 19 |
| 4,479,012 | 10/1984 | Fischer et al. | 203/91 |
| 4,802,956 | 2/1989 | Dornhagen et al. | 203/DIG. 19 |
| 4,950,800 | 8/1990 | Weber et al. | 568/492 |

FOREIGN PATENT DOCUMENTS

| | | | |
|---|---|---|---|
| 373443 | 6/1990 | European Pat. Off. | 568/492 |
| 56-83433 | 7/1981 | Japan | 568/492 |
| 487056 | 12/1975 | U.S.S.R. | 568/492 |
| 927792 | 5/1982 | U.S.S.R. | 568/492 |
| 988804 | 1/1983 | U.S.S.R. | 568/492 |

*Primary Examiner*—Wilbur Bascomb, Jr.
*Attorney, Agent, or Firm*—Reynold J. Finnegan

[57] ABSTRACT

A method for distilling a crude aldehyde product mixture of branched chain and straight chain aldehyde in a single distillation column to concurrently obtain three separate product streams, i.e. a purified branched chain aldehyde stream and two different purified straight chain aldehyde streams.

7 Claims, 1 Drawing Sheet

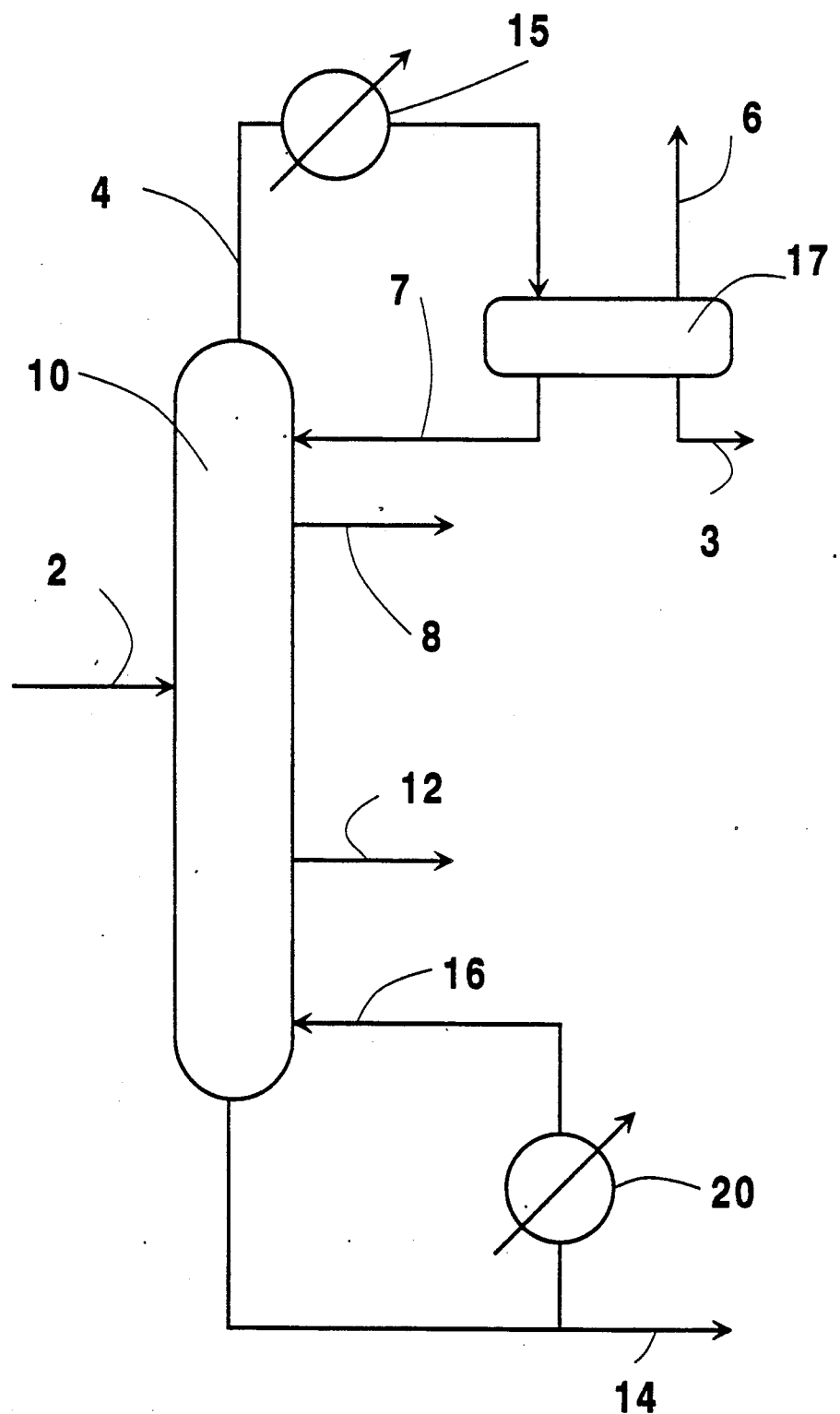

MIXED ALDEHYDE PRODUCT SEPARATION BY DISTILLATION

FIELD OF THE INVENTION

This invention is directed to a method for refining a crude aldehyde product mixture in order to concurrently and separately recover both branched chain aldehyde and straight chain aldehyde therefrom. More preferably this invention is directed to the distillation a crude aldehyde product mixture of branched chain and straight chain aldehydes in a single distillation column to concurrently obtain three separate product streams, i.e. a purified branched chain aldehyde stream and two different purified straight chain aldehyde streams.

BACKGROUND OF THE INVENTION

Methods for producing aldehydes by the hydroformylation of an olefinically unsaturated organic compound with carbon monoxide and hydrogen (more commonly referred to as synthesis or syn gas) in the presence of a rhodium-phosphorus complex catalyst and free phosphorus ligand are well known in the art as seen; e.g., by the basic low pressure oxo hydroformylation process of U.S. Pat. No. 3,527,809 and the rhodium-catalyzed gas and liquid recycle hydroformylation processes of U.S. Pat. Nos. 4,148,830; 4,247,486 and 4,593,127. The resultant aldehyde products are mixtures of normal (straight chain) and iso (branched chain) aldehydes corresponding to the olefin starting material and result from adding a formyl group (—CHO) at one of the carbon atoms of an ethylenic group (e.g. —CH=CH$_2$) of the olefin. For instance, the hydroformylation of propylene produces n-butyraldehyde [CH$_3$CH$_2$CH$_2$CHO] and iso-butyraldehyde [CH$_3$CH(CHO)CH$_3$]. In general such hydroformylation processes are preferably designed to produce aldehyde products rich in the normal (straight chain) isomer.

Moreover as taught in U.S. Pat. Nos. 4,148,830 and 4,247,486 such continuous hydroformylation processes inherently produce high boiling liquid aldehyde condensation by-products, e.g. dimers, trimers and tetramers, which may serve as a solvent for the hydroformylation process, as well as other liquid heavies. Thus a small amount of such higher boilers is always invariably contained in the crude aldehyde product mixture obtained even after separating the initial aldehyde product from its lights (e.g. carbon monoxide, hydrogen, unreacted alkylene, alkane by-product, etc.) as in the case of a continuous gas recycle hydroformylation process or after separating the initial aldehyde product from its lights and catalyst containing solution as in the case of a continuous liquid recycle hydroformylation process. Indeed even after separating the lower boiling, branched chain aldehyde from its higher boiling normal straight chain aldehyde counterpart in order to obtain purified branched chain aldehyde (e.g. iso-butyraldehyde) and leave the straight chain aldehyde (e.g. n-butyraldehyde), the normal aldehyde product may still contain a higher amount of such organic heavies than desired for its eventual end-use.

Accordingly, heretofore, it has been the conventional procedure in the art to refine and separate the branched-chain aldehyde product from the straight chain aldehyde product of such crude aldehyde product mixtures resulting from such conventional continuous rhodium catalyzed hydroformylation processes by a two step distillation procedure that involves the use of two separate distillation columns. For example, purified branched chain aldehyde (e.g. iso-butyraldehyde) is first separated from the crude aldehyde product mixture via distillation in an initial distillation column and then the remaining normal (straight chain) aldehyde (e.g. n-butyraldehyde) is further refined or purified from any remaining higher boiling by-products by a second distillation carried out in a second distillation column.

However, there are two major penalties associated with commercially refining the crude aldehyde product mixture via such a dual distillation procedure. The first is the very high energy cost required to operate such dual distillation procedures on a commercial level. Secondly, a significant amount of aldehyde is lost due to in situ conversion into such heavies during such distillation procedures because of the high temperatures employed to recover as much straight chain aldehyde from said organic heavies as possible. Indeed, it has been estimated that as much as 1 to 2 percent by weight or more of straight chain aldehyde may be lost by its own in situ conversion to heavies and such is clearly a significant amount in any commercial operation, such as the above discussed hydroformylation operations, that may produce hundreds of millions of pounds of aldehyde per year.

In a previous commercial operation conducted more than a year prior to the filing of this application at a plant in the United States, owned and operated by assignee, applicant experimented with employing a single distillation column, wherein purified branched chain iso-butyraldehyde was obtained by distilling same overhead and essentially all of the straight chain n-butyraldehyde was collected as a distilled gas from a lower side vent off of the same distillation column. However, as in the case with conventional two stage distillation procedures that involve two distillation columns, the distillation temperature required to obtain essentially all of the n-butyraldehyde off the side vent of the single distillation column was essentially the same high distillation temperature (e.g. about 115° C. to about 140° C.) conventionally employed in distilling n-butyraldehyde from organic heavies in a second distillation column, thus causing essentially the same type of detrimental loss of aldehyde due to in situ heavies formation as normally occurs with a second distillation column.

It has now been discovered that it is not necessary to employ such high distillation temperatures in order to concurrently separate and obtain both purified branched chain aldehyde and purified straight chain aldehyde from a crude aldehyde product mixture using a single distillation column. Thus such drawbacks associated with heretofore conventional distillation refining of crude aldehyde product mixtures may be overcome or at least greatly minimized by the process of this invention and explained more fully below.

SUMMARY OF THE INVENTION

Thus it is an object of this invention to provide a novel method for refining a crude aldehyde product mixture containing branched chain and straight chain aldehyde, which comprises concurrently obtaining and separating purified branched chain aldehyde and purified straight chain aldehyde by distilling said crude aldehyde product mixture using a single distillation column.

Accordingly, a generic aspect of this invention may be described as a process for refining a liquid crude aldehyde product mixture consisting essentially of from about 95 to about 99.95 percent by weight of straight chain and branched chain aldehydes selected from the group consisting of $C_4$ aldehydes and $C_5$ aldehydes, based on the total weight of said product mixture, the remainder consisting essentially of organic heavies, said process comprising adding said liquid crude aldehyde product mixture starting material to a distillation column and distilling said liquid crude aldehyde product mixture in said distillation column, at a base temperature of from about 1° C. to about 35° C. above the normal boiling point of the straight chain aldehyde present in said liquid aldehyde product mixture starting material, so as to concurrently obtain (i) a liquid aldehyde product stream taken from at or near the top of the distillation column and consisting essentially of purified branched chain aldehyde and (ii) a volatilized aldehyde product stream consisting essentially of purified straight chain aldehyde in an amount of no more than about 70 percent by weight of the amount of straight chain aldehyde present in said liquid crude aldehyde product mixture starting material, and less than 33 percent by weight of the amount of organic heavies present in said liquid crude aldehyde product mixture starting material, and (iii) wherein the remaining purified liquid aldehyde consisting essentially of straight chain aldehyde is recovered from at or near the bottom of the distillation column, and wherein the amount of organic heavies present in the recovered purified liquid aldehyde is less than about 1 percent by weight of the total amount of aldehyde fed to the distillation column plus at least about 67 percent by weight of the amount of organic heavies present in the liquid crude aldehyde product mixture starting material.

BRIEF DESCRIPTION OF THE DRAWING

The drawing is a schematic flow diagram of the subject invention illustrating the embodiment of a distillation column (10) for distilling a crude aldehyde product mixture (line 2) to effect the concurrent recovery of purified- branched chain aldehyde liquid product (line 8) at or near the top of the column and purified straight chain aldehyde as a vapor stream (line 12) from the side of the column, the second purified aldehyde product (line 14) exiting at or near the bottom of the column.

DESCRIPTION OF THE PREFERRED EMBODIMENTS

The crude aldehyde liquid product mixture employed herein may be obtained from any conventional metal (preferably rhodium complex) catalyzed hydroformylation process conducted in the presence of free organic phosphorus ligand. Such oxo processes and the conditions thereof are well known in the art as illustrated by the continuous liquid and gas recycle processes of U.S. Pat. Nos. 4,148,830; 4,247,486; 4,593,127 and U.S. patent application Ser. No. 370,806 filed June 23, 1989, now U.S. Pat. No. 5,001,275 patented Mar. 19 1991, the entire disclosures of which are incorporated herein by reference thereto. Such hydroformylation processes in general involve the production of aldehydes rich in their normal straight chain isomers by reacting an olefinic compound with hydrogen and carbon monoxide in a liquid reaction medium which contains the aldehyde product, a soluble rhodium-organophosphorus complex catalyst, free organophosphorus ligand and higher boiling aldehyde condensation by-products.

Of course, it is to be understood that the particular manner in which the hydroformylation reaction is carried out and particular hydroformylation reaction conditions employed are not critical to the subject invention and may be varied widely and tailored to meet individual needs and to produce the particular aldehyde product desired.

Accordingly, the olefinic starting material reactants of the hydroformylation process from which the crude liquid aldehyde product starting materials of this invention may be derived can contain 3 or 4 carbon atoms. Illustrative olefins are propylene, 1-butene, 2-butene (cis or trans), and 2-methyl propene (isobutylene). Of course, it is understood that mixtures of different olefinic starting materials could be employed, if desired. For example, it is common place to sometimes employ a mixture of 1-butene and 2-butene as the starting olefin. The most preferred olefin is propylene.

Likewise, any conventional rhodium-phosphorus complex catalyst could be employed and such catalysts as well as methods for their preparation are well known in the art. Such rhodium-phosphorus complex catalysts may include any rhodium-organophosphorus complex, such as the rhodium-organophosphine or rhodium-organophosphite complex hydroformylation catalysts heretofore advanced for such hydroformylation processes. Of course, mixtures of such catalysts could also be employed, if desired. Moreover, it is clear that the amount of complex catalyst present in the reaction medium of a given process need only be that minimum amount necessary to provide the rhodium metal concentration desired to be employed and which will furnish the basis for at least that catalytic amount of rhodium metal necessary to catalyze the particular hydroformylation process desired. In general, rhodium metal concentrations in the range of from about 10 ppm to about 1000 ppm, calculated as free metal, should be sufficient for most hydroformylation processes. It is generally preferred to employ from about 10 to 700 ppm of rhodium, and more preferably, from 25 to 500 ppm of rhodium, calculated as free metal.

As noted above, the hydroformylation process is carried out in the presence of free phosphorus ligand, i.e., ligand that is not complexed with the rhodium complex catalyst employed. However, while it is generally preferred that the free phosphorus ligand be the same as the phosphorus ligand of the rhodium-phosphorus complex catalyst, such is not necessary and different ligands could be employed in a given process, if desired. Accordingly, as in the case of the rhodium-organophosphorus complex catalyst, any conventional organophosphorus ligand could be employed as the free ligand and such ligands, as well as methods for their preparation, are well known in the art. Such free phosphorus ligands may include any of the organophosphine or organophosphite ligands heretofore advanced for such hydroformylation processes. Of course, mixtures of such ligands can also be employed, if desired. Thus, the hydroformylation process may be carried out in any excess amount of free phosphorus ligand, e.g., at least one mole of free phosphorus ligand per mole of rhodium metal present in the reaction medium. The amount of free phosphorus ligand employed, in general, merely depends upon the aldehyde product desired, and the olefin and complex catalyst employed. Accordingly, amounts of free phosphorus ligand present in the reaction medium ranging from about 2 to about 300 or more per mole of rhodium present should be suitable for most purposes. For example, in general, large amounts of free triarylphosphine ligand, e.g., triphenylphosphine, such as more than 50 moles, or more preferably, more than 100 moles of free ligand per mole of rhodium have preferably been employed to achieve satisfactory catalytic activity and/or catalyst stabilization, while other organophosphorus ligands, e.g., alkylarylphosphines and cycloalkylarylphosphines and/or organophosphites may help provide acceptable catalyst stability and reactivity without unduly retarding the conversion rates of certain olefins to aldehydes when the amount of free ligand present in the reaction medium is as little as 1 to 100 and, more preferably, 15 to 60 moles per mole of rhodium present. More particularly, illustrative rhodium-phosphorus complex catalysts and illustrative free phosphorus ligands include, e.g., those disclosed in U.S. Pat. Nos. 3,527,809; 4,148,830; 4,247,486; 4,283,562; 4,400,548; 4,482,749; 4,496,748; 4,599,206; 4,668,651; 4,716,250; 4,717,775; 4,731,486; 4,737,588; 4,748,261; 4,769,498; 4,774,361; 4,885,401; PCT patent application, Publication No. WO 80/01690 (published Aug. 21, 1980). Among the more preferred ligands and complex catalysts that may be mentioned are, e.g., the triphenylphosphine ligand and rhodium-triphenylphosphine complex catalysts of U.S. Pat. Nos. 3,527,809 and 4,148,830 and 4,247,486; the alkylphenylphosphine and cycloalkylphenylphosphine ligands, and rhodium-alkylphenylphosphine and rhodium-cycloalkylphenylphosphine complex catalysts of U.S. Pat. No. 4,283,562; and the organophosphite ligands and rhodium-organophosphite complex catalysts of U.S. Pat. No. 4,599,206; 4,737,588; 4,717,775; 4,774,361; 4,668,651 and 4,748,261. The most preferred ligand is triphenylphosphine (TPP), while the preferred catalyst is a rhodium-TPP complex.

As further noted above, the hydroformylation reaction is carried out in the presence of higher boiling aldehyde condensation by-products. It is the nature of such continuous hydroformylation reactions to produce such higher boiling aldehyde by-products (e.g., dimers, trimers and tetramers) in situ during the hydroformylation process as explained more fully, e.g. in U.S. Pat. No. 4,148,830; 4,247,486; and 4,593,127 and U.S. application Ser. No. 370,806 filed June 23, 1989. Such aldehyde by-products provide an excellent carrier for the liquid catalyst recycle process. Indeed, while one may employ, if desired, any suitable solvent at the start-up of a continuous process (aldehyde compounds corresponding to the desired aldehyde products being preferred), the primary solvent will normally eventually comprise both aldehyde products and higher boiling aldehyde condensation by-products due to the nature of such continuous processes. Of course, aldehyde condensation by-products can also be preformed if desired and used accordingly. It is also obvious that the amount of such higher boiling aldehyde by-products present in the reaction medium may vary over wide limits and is generally governed only by equipment constraints and the particular aldehyde product to be produced. For example, initially the hydroformylation reaction can be effected in the absence or in the presence of small amounts of higher boiling aldehyde condensation by-products as a solvent for the rhodium complex catalyst, or the reaction can be conducted in the presence of upwards of 70 weight percent, or even as much as 90 weight percent, and more of such condensation by-products, based on the total liquid reaction medium. In general, ratios of aldehyde to higher boiling aldehyde condensation by-products within the range of from about 1:4 to about 20:1 by weight should be sufficient for most purposes. Likewise it is to be understood that minor amounts of other conventional organic cosolvents may be present if desired.

While the hydroformylation reaction conditions may very over wide limits, as discussed above, in general it is more preferred that the process be operated at a total gas pressure of hydrogen, carbon monoxide and olefinic unsaturated starting compound of less than about 1500 psia, preferably less than about 450 psia and more preferably less than about 350 psia. The minimum total pressure of the reactants is not particularly critical and is limited mainly only by the amount of reactants necessary to obtain a desired rate of reaction. More specifically, the carbon monoxide partial pressure of the hydroformylation process of this invention is preferably from about 1 to about 120 psia and, more preferably, from about 3 to about 90 psia, while the hydrogen partial pressure is preferably from about 10 to about 160 psia and more preferably from about 15 to about 100 psia. In general $H_2:CO$ molar ratio of gaseous hydrogen to carbon monoxide may range from about 1:10 to about 100:1 or higher, the more preferred hydrogen to carbon monoxide molar ratio being from about 1:1 to about 50:1.

Further, as noted above, the hydroformylation process may be conducted at a reaction temperature from about 50° C. to about 145° C. However, in general, hydroformylations at reaction temperatures of about 60° C. to about 120° C. and more preferably about 75° C. to about 115° C. are preferred.

Thus as noted herein the crude aldehyde liquid product mixtures employable as the starting materials of this invention consist essentially of aldehydes and organic heavies and possibly some of the free organic phosphorus ligand employed in the hydroformylation process; preferably obtained after separating the initial aldehyde product from its lights (e.g. compounds having boiling points below that of the aldehyde product compounds) in the case of a continuous gas recycle hydroformylation process or after separating the initial aldehyde product from its lights and catalyst containing solution as in the case of a continuous liquid recycle hydroformylation process.

As noted above the aldehydes in the crude aldehyde product mixture employable herein are dependent upon the olefin starting material of the hydroformylation process from whence said product mixtures are derived and such aldehydes may contain 4 or 5 carbon atoms, such as the $C_4$ and $C_5$ aldehydes derived from propylene and butylene, respectively. Moreover it is understood that such aldehydes are produced as mixtures of both normal (straight chain) and iso (branched chain) aldehydes. Thus illustrative aldehyde products include the $C_4$ aldehyde mixtures of n-butyraldehyde (n-butanal) and iso-butyraldehyde (iso-butanal), and the $C_5$ aldehyde mixtures of n-valeraldehyde (n-pentanal) and isomer branched-chain pentanals, i.e. 2-methyl butyraldehyde, 3-methyl butyraldehyde and/or pivaldehyde. Said aldehyde mixtures may contain normal to branched chain isomer aldehyde molar ratios of from about 1:1, to as high as about 50:1, or higher, the upper limit of richness in normal aldehyde being governed only by the hydroformylation process that furnishes the crude aldehyde product mixture starting material.

Likewise the organic heavies contained in the crude aldehyde product mixtures employable herein include any organic solvent and organic by-product having boiling points above that of the straight chain aldehyde product compounds of the hydroformylation process from whence said product mixtures are derived, such as the liquid aldehyde condensation by-products (dimers, trimers, tetramers, etc.), discussed above, e.g. in U.S. Pat. No. 4,148,830, and other common higher boiler by-product, e.g. corresponding alkanol. Of course it is understood that such crude aldehyde product mixtures can also contain some minor amounts of residual lights (e.g. unreacted olefin and by-product alkane) and organophosphorus contaminant e.g. free organophosphorus ligand and/or its corresponding oxide, and alkyl substituted phosphorus compounds, that may be present as a result of their in situ formation or deliberate use in the hydroformylation process.

For instance the crude liquid aldehyde product mixture starting materials employable herein can be derived from a gas recycle hydroformylation process such as described in the above cited patents and preferably illustrated by U.S. Pat. No. 4,247,486, and the reference article in *INDICATIONS*, Winter, 1982/83, The International Journal of Davy McKee, pp 1 and 20 to 28, published by the public affairs department of the Davy Corporation, London, England. Likewise the crude liquid aldehyde product mixture employable herein can be derived from a liquid catalyst recycle process as described in the above cited patents and preferably illustrated e.g. by the primary reactor system of FIG. 1 of U.S. Pat. No. 4,593,127, Canadian Patent No. 1,202,326 and assignee's U.S. application, Ser. No. 370,806 filed June 23, 1989, now U.S. Pat. No. 5,001,275, as well as applicants concurrently filed U.S. application, Ser. No. 611,081, entitled IMPROVED HYDROFORMYLATION PROCESS directed to a novel method for separating lights from the aldehyde product mixture, the entire disclosure of which applications are encompassed herein by reference thereto. Preferably the crude aldehyde liquid product mixtures employable herein are derived from liquid catalyst recycle hydroformylation processes. Moreover, as seen by said prior art, and as the case with gas recycle processes, it is preferred to remove at least the majority of lights from the aldehyde product mixture of a liquid catalyst recycle process, prior to separating the branched chain aldehyde isomer from the higher boiling straight chain aldehyde. However regardless of what type of purification steps may or may not have been undertaken to separate lights and/or organophosphorus contaminates from the crude aldehyde product mixture obtained from a liquid catalyst recycle process, it is preferred to pass the crude aldehyde product mixture through a stabilizer such as shown by column 7 of the drawing on page 23 of the above *INDICATIONS* article before employing the crude aldehyde product mixture as the liquid starting material of the process of this invention.

Thus, the crude aldehyde liquid product mixture employable herein may consist essentially of from about 95 to about 99.95 weight percent, preferably about 97 to about 99.95 weight percent aldehyde, based on the total weight of said liquid product mixture; the remainder of said liquid product mixture consisting essentially of organic heavies.

Accordingly referring to the accompanying drawing which schematically shows the present invention, the refining process of this invention may be carried out in any suitable distillation column having two side vents to draw off liquid and vaporized streams of aldehyde product. Thus said distillation column includes any distillation or packed column or other suitable vaporizer apparatus (10) in which the subject distillation may take place. For example, see "Chemical Engineering Handbook," Perry and Chilton, 5th Edition, page 13-3 FIG. 13-1, page 13-19 FIG. 13-18, and page 13-50; also "Unit Operations in Chemical Engineering," McCabe and Smith, 3rd Edition, page 548. The actual type of packing or trays in the column is not a critical part of this invention and any type of tray or packing may be used. In addition the number of trays or separation stages used is not critical and need only be sufficient to effect the desired separations. Thus the liquid crude aldehyde product mixture starting material (line 2) is introduced to the distillation column in the normal fashion for separating close-boiling isomers, such as n-butyraldehyde and iso-butyraldehyde, e.g. at a point some distance from both the top and the bottom of the column, preferably somewhere around the middle of the column. Again the exact point where the aldehyde product mixture starting material is introduced is not critical to the invention and can be preferably determined by standard engineering practice.

The liquid crude aldehyde product mixture starting material is then distilled to concurrently remove both purified liquid branched-chain iso-aldehyde and purified straight chain normal aldehyde, as well as lights therefrom. For instance vaporized lights (i.e. materials having a boiling point below the branched chain aldehyde, e.g. unreacted olefin, alkane, etc.) are taken overhead (line 4) where they may be cooled (cooler 15) and partially or completely condensed (catchpot 17) as desired. The non-condensables are purged (line 6) and the condensables e.g. water, recovered or purged (line 3). In addition, if desired, some of the condensed overhead can be returned to the column (via line 7) to serve as reflux.

The purified branched chain iso-aldehyde (which is lighter, i.e. has a lower boiling point, than the straight chain normal aldehyde), may be removed at or near the top of the distillation column. Preferably said branched chain iso-aldehyde is removed as a liquid side stream (line 8), somewhere above the liquid crude aldehyde product mixture starting material feed point. The exact point is not critical and the preferred point can be determined by standard engineering practice.

Concurrently purified vaporized straight chain, normal aldehyde is removed as a vapor sidestream (line 12) somewhere below the liquid crude aldehyde product mixture starting material feed point. Again the exact point for such removal is not critical, and the preferred point can be determined by standard engineering practice. Further if desired a vapor entrainment separator (not shown) can be used to return any liquids from the vaporized straight chain aldehyde stream to the column, however such an entrainment separator is not a necessary or essential part of the embodiment of the process of this invention.

The remaining purified liquid aldehyde is recovered (line 14) from at or near the bottom of the column. Further if desired part of the straight chain aldehyde leaving the bottom of the column can be heated in a reboiler (20) and returned to the column. The liquid bottom aldehyde product consists essentially of straight chain aldehyde and the amount of organic heavies present in said recovered purified liquid aldehyde is less than about 1 percent by weight of the total amount of aldehyde fed to the distillation column plus at least about 67 percent by weight of the amount of organic heavies present in the liquid crude aldehyde product mixture starting material.

The distillation of the liquid crude aldehyde product mixture starting material in the refining process of this invention may take place under such conditions as a base temperature in the distillation column in the range of from about 1° C. to about 35° C., preferably from about 10° C. to about 35° C., above the normal boiling point (i.e., at 14.7 psia.) of the straight chain aldehyde in the liquid crude aldehyde product mixture starting material, and at a top pressure in the distillation column in the range of from about 1 psig to about 30 psig, preferably from about 1 psig to about 15 psig. The conditions (e.g. temperature, pressure, reflux rate, etc.) at the top part of the distillation zone wherein vaporized lights and branched chain aldehyde are removed are not narrowly critical and are primarily merely dependent only upon obvious practical processing conditions required to achieve the desired result of removing such lights and obtaining said liquid aldehyde side stream consisting essentially of at least 99 percent by weight of branched chain aldehyde and less than about 1 percent by weight of the amount of organic heavies present in the liquid crude aldehyde product mixture starting material. Moreover, preferably the amount of liquid branched chain aldehyde so obtained is essentially equal to that amount of branched chain aldehyde present in the liquid crude aldehyde product mixture starting material. Of course, it is to be understood that the heat required for distillation of the aldehyde compounds may be supplied by any conventional heat exchanger. Further, it is to be understood that while the most optimum conditions of the subject invention necessary to achieve the best results and efficiency desired are dependent upon one's experience in the utilization of the subject invention, only a certain measure of experimentation should be necessary to ascertain those conditions which are optimum for a given situation and such should be well within the knowledge of one skilled in the art and easily obtainable by following the more preferred aspects of this invention as explained herein and/or by simple routine experimentation. For instance, in general higher distillation pressures will require higher temperatures and lower pressures will require lower temperatures.

In general, it is preferred to correlate the base temperature and pressure conditions in the process of this invention so that the amount of purified volatilized straight chain aldehyde obtained via said side stream is no more than about 70 percent of the amount of straight chain aldehyde present in the liquid crude aldehyde product mixture starting material and wherein said purified volatilized straight chain aldehyde contains less than about 33 percent by weight of the amount of organic heavies present in said liquid crude aldehyde product mixture starting material. Accordingly, the base conditions are preferably correlated so that at least about 5 to no more than 70 percent by weight of the straight chain aldehyde present in the liquid crude aldehyde product mixture starting material is removed and obtained via said vaporized straight chain aldehyde side stream. Likewise, said conditions are also so preferably correlated that said purified volatilized straight chain aldehyde so obtain may contain from 0 to about 33 percent by weight of the amount of organic heavies present in the liquid crude aldehyde product mixture starting material. More preferably said purified straight chain aldehyde so obtained contains less than about 10 percent by weight of the amount of organic heavies present in the liquid crude aldehyde product mixture starting material.

The remaining purified liquid aldehyde product may easily be removed and recovered as a liquid stream from the bottom of the distillation column and consists essentially of straight chain aldehyde amounting to from about 30 to about 95 percent by weight of the amount of straight chain aldehyde present in the liquid crude aldehyde product mixture starting material and the amount of organic heavies present in said recovered purified liquid aldehyde is less than about 1 percent by weight of the total amount of aldehyde feed to the distillation column plus at least about 67 percent by weight, preferably at least about 90 percent by weight, of the amount of organic heavies present in the liquid crude aldehyde product mixture starting material.

The refining process of this invention is indeed unique in that it provides for not only a very high energy cost savings due to the elimination of such above-described heretofore conventional dual distillation procedures, but also eliminates or at least greatly minimizes the above-discussed loss in aldehyde due to its in situ conversion to organic heavies that is attendant with such prior distillation procedures, while also providing for the recovery of three different purified aldehyde product streams from a single distillation column.

Of course, it is elementary that the hydroformylated aldehyde products have many well-known and conventional utilities. Most preferably, such aldehyde products are further conventionally employed to produce alcohols and other useful solvents.

The following examples are illustrative of the present invention and are not to be regarded as limitive. It is to be understood that all parts, percentages and proportions referred to herein and in the appended claims are by weight unless otherwise indicated, the given amount of rhodium being calculated as free metal.

EXAMPLE 1

The following computerized (calculated) experiment demonstrates the subject invention. In accordance with the drawing, about 18,600 lbs/hr of crude mixed normal and iso- butyraldehyde containing about 0.2% by weight components lighter than isobutyraldehyde and about 0.4% by weight components heavier than normal butyraldehyde is fed as stream 2 to the 61st theoretical tray from the bottom of a distillation column having 105 theoretical trays. Light impurities along with some branched aldehyde are removed from the top of the column, partially condensed by cooler 15, and collected in catchpot 17. Some of the resulting liquid stream is returned to the column for reflux as stream 7; about 200 lb/hr are removed from the system as purge streams 3 and 6. A liquid sidestream of about 2,100 lb/hr is taken from the 103rd theoretical tray from the bottom as isobutyraldehyde product (stream 8). A vapor sidestream of about 7,200 lb/hr is taken from the 3rd theoretical tray from the bottom as high purity normal butyraldehyde product (stream 12). This vapor stream passes through a small entrainment separator (not shown) to remove any entrained liquid from the vapor stream. A liquid stream of about 9,100 lbs/hr is taken off the bottom of the column as a second purified normal butyraldehyde product (stream 14). The base distillation temperature of the column is about 99° C., and the pressure at the top of the distillation column is about 10 psig. The isobutyraldehyde content of the upper sidestream (8) is about 99.9% by weight; the heavies content of the normal butyraldehyde bottoms stream (14) is about 0.93% by weight; the ratio of the heavies concentration in the feed to the heavies concentration in the lower vapor sidestream (12) is about 300:1. The heavies content of stream 14 is essentially equal to about 100% by weight of the heavies content of stream 2 plus about 0.1% by weight of the mixed aldehyde content of stream 2.

EXAMPLE 2

The following actual operating data from a commercial system is given to demonstrate the subject invention. In accordance with the drawing, about 20,000 lbs/hr of crude mixed normal and isobutyraldehyde containing about 0.01% by weight components lighter than isobutyraldehyde and about 0.4% by weight components heavier than normal butyraldehyde was fed as stream 2 to the 61st theoretical tray from the bottom of a distillation column having 105 theoretical trays. Light impurities along with some branched chain aldehyde were removed from the top of the column, partially condensed by cooler 15, and collected in catchpot 17. Some of the resulting liquid was returned to the column for reflux as stream 5; about 200 lb/hr were removed from the system as purge streams 3 and 6. A liquid sidestream of about 2,175 lb/hr was taken from the 103rd theoretical tray from the bottom as isobutyraldehyde product (stream 8). A vapor sidestream of about 5,000 lb/hr was taken from the 3rd theoretical tray from the bottom as high purity normal butyraldehyde product (stream 12). This vapor stream passed through a small entrainment separator (not shown) to remove any entrained liquid from the vapor stream. A liquid stream of about 12,625 lbs/hr was taken off the bottom of the column as a second purified normal butyraldehyde product (stream 14). The base distillation temperature of the column was about 105° C., and the pressure at the top of the distillation column was about 8.5 psig. The isobutyraldehyde content of the upper sidestream (8) was about 99.6% by weight; the heavies content of the normal butyraldehyde bottoms stream (14) was about 0.7% by weight; the ratio of the heavies concentration in the feed to the heavies concentration in the lower vapor sidestream (12) was about 36:1. The heavies content of stream 14 was essentially equal to about 100% by weight of the heavies content of stream 2 plus about 0.04% by weight of the mixed aldehyde content of stream 2.

EXAMPLE 3

The following computerized (calculated) experiment demonstrates the subject invention. In accordance with the drawing, about 18,950 lbs/hr of crude mixed normal and iso- butyraldehyde containing about 0.2% by weight components lighter than isobutyraldehyde and about 2.6% by weight components heavier than normal butyraldehyde is fed as stream 2 to the 61st theoretical tray from the bottom of a distillation column having 105 theoretical trays. Light impurities along with some branched aldehyde are removed from the top of the column, partially condensed by cooler 15, and collected in catchpot 17. Some of the resulting liquid stream is returned to the column for reflux as stream 7; about 240 lb/hr are removed from the system as purge streams 3 and 6. A liquid-sidestream of about 2,050 lb/hr is taken from the 103rd theoretical tray from the bottom as isobutyraldehyde product (stream 8). A vapor sidestream of about 7,200 lb/hr is taken from the 3rd theoretical tray from the bottom as high purity normal butyraldehyde product (stream 12). This vapor stream passes through a small entrainment separator (not shown) to remove any entrained liquid from the vapor stream. A liquid stream of about 9,460 lbs/hr is taken off the bottom of the column as a second purified normal butyraldehyde product (stream 14). The base distillation temperature of the column is about 101° C., and the pressure at the top of the distillation column is about 10 psig. The isobutyraldehyde content of the upper sidestream (8) is about 99.8% by weight; the heavies content of the normal butyraldehyde bottoms stream (14) is about 6.1% by weight; the ratio of the heavies concentration in the feed to the heavies concentration in the lower vapor sidestream (12) is about 161:1. The heavies content of stream 14 is essentially equal to about 100% by weight of the heavies content of stream 2 plus about 0.45% by weight of the mixed aldehyde content of stream 2.

EXAMPLE 4

The following computerized (calculated) experiment demonstrates the subject invention. In accordance with the drawing, about 22,200 lbs/hr of crude mixed normal and branched chain pentanals containing about 0.1% by weight components lighter than the branched pentanals and about 0.3% by weight components heavier than normal pentanal is fed as stream 2 to the 61st theoretical tray from the bottom of a distillation column having 105 theoretical trays. Light impurities along with some branched aldehyde are removed from the top of the column, partially condensed by cooler 15, and collected in catchpot 17. Some of the resulting liquid stream is returned to the column for reflux as stream 5; about 200 lb/hr are removed from the system as purge streams 3 and 6. A liquid sidestream (stream 8) of about 6,700 lb/hr is taken from the 103rd theoretical tray from the bottom as branched aldehyde product (essentially 2-methyl butyraldehyde). A vapor sidestream of about 4,300 lb/hr is taken from the 3rd theoretical tray from the bottom as high purity normal pentanal product (stream 12). This vapor stream passes through a small entrainment separator (not shown) to remove any entrained liquid from the vapor stream. A liquid stream of about 11,000 lbs/hr is taken off the bottom of the column as a second purified normal pentanal product (stream 14). The base distillation temperature of the column is about 129° C., and the pressure at the top of the distillation column is about 10 psig. The branched aldehyde content of the upper sidestream (8) is about 99.8% by weight; the heavies content of the normal pentanal bottoms stream (14) is about 0.7% by weight; the ratio of the heavies concentration in the feed to the heavies concentration in the lower vapor sidestream (12) is about 4:1. The heavies content of stream 14 is essentially equal to about 100% by weight of the heavies content of stream 2 plus about 0.05% by weight of the mixed aldehyde content of stream 2.

Various modifications and variations of this invention will be obvious to a worker skilled in the art and it is to be understood that such modifications and variations are within the purview of this application and the spirit and scope of the appended claims.

What is claimed is:

1. A process for refining a liquid crude aldehyde product mixture consisting essentially of from about 95 to about 99.95 percent by weight of straight chain and branched chain aldehydes selected from the group consisting of $C_4$ aldehydes and $C_5$ aldehydes, based on the total weight of said product mixture, the remainder consisting essentially of organic heavies, said process comprising adding said liquid crude aldehyde product mixture starting material to a distillation column and distilling said liquid crude aldehyde product in said distillation column, at a base temperature of from about 1° C. to about 35° C. above the normal boiling point of the straight chain aldehyde present in said liquid aldehyde product mixture starting material, so as to concurrently obtain (i) a liquid aldehyde product stream taken from at or near the top of the distillation column and consisting essentially of purified branched chain aldehyde and (ii) a volatilized aldehyde product stream consisting essentially of purified straight chain aldehyde in an amount of no more than about 70 percent by weight of the amount of straight chain aldehyde present in said liquid crude aldehyde product mixture starting material, and less than 33 percent by weight of the amount of organic heavies present in said liquid crude aldehyde product mixture starting material, and (iii) wherein the remaining purified liquid aldehyde consisting essentially of straight/chain aldehyde is recovered from at or near the bottom of the distillation column, and wherein the amount of organic heavies present in the recovered purified liquid aldehyde is less than about 1 percent by weight of the total amount of aldehyde fed to the distillation column plus at least about 67 percent by weight of the amount of organic heavies present in the liquid crude aldehyde product mixture starting material.

2. A process as defined in claim 1, wherein the distillation is carried out at a base temperature of from about 10° C. to about 35° C. above the normal boiling point of said straight chain aldehyde.

3. A process as defined in claim 2, wherein the aldehydes of said crude aldehyde product mixture starting material are n-butanal and iso-butanal.

4. A process as defined in claim 2, wherein the aldehydes of said crude aldehyde product mixture starting material are n-pentanal and branched chain pentanals.

5. A process as defined in claim 1, wherein the distillation is carried out at a top pressure of from about 1 to 30 psig.

6. A process as defined in claim 3, wherein the distillation is carried out at a top pressure of from about 1 to 15 psig.

7. A process as defined in claim 4, wherein the distillation is carried out at a top pressure of from about 1 to 15 psig.

* * * * *